United States Patent [19]

Wardle

[11] Patent Number: 4,688,555
[45] Date of Patent: Aug. 25, 1987

[54] ENDOSCOPE WITH CABLE COMPENSATING MECHANISM

[75] Inventor: John L. Wardle, Shelton, Conn.

[73] Assignee: Circon Corporation, Santa Barbara, Calif.

[21] Appl. No.: 856,677

[22] Filed: Apr. 25, 1986

[51] Int. Cl.⁴ .............................................. A61B 1/00
[52] U.S. Cl. ..................................................... 128/4
[58] Field of Search .......................... 128/4, 5, 6, 7, 8; 138/120, 118

[56] References Cited

U.S. PATENT DOCUMENTS

| | | | |
|---|---|---|---|
| 3,162,214 | 12/1964 | Bazinet, Jr. | 128/4 X |
| 3,266,059 | 8/1966 | Stelle | 128/4 X |
| 3,270,641 | 9/1966 | Gosselin | 128/4 X |
| 3,557,780 | 1/1971 | Sato | 128/4 |
| 3,610,231 | 10/1971 | Takahashi et al. | 128/6 |
| 3,788,303 | 1/1974 | Hall | 128/4 |
| 3,892,228 | 7/1975 | Mitsui | 128/4 |
| 4,066,071 | 1/1978 | Nagel | 128/7 |
| 4,108,211 | 8/1978 | Tanaka | 128/4 X |
| 4,207,873 | 6/1980 | Kruy | 128/6 |
| 4,236,509 | 12/1980 | Takahashi et al. | 128/4 |
| 4,273,111 | 6/1981 | Tsukaya | 128/6 |
| 4,301,790 | 11/1981 | Bol et al. | 128/6 |
| 4,401,123 | 8/1983 | Baba | 128/6 |
| 4,417,583 | 11/1983 | Bechai et al. | 128/4 X |
| 4,483,326 | 11/1984 | Yamaka et al. | 128/4 |
| 4,499,895 | 2/1985 | Takayama | 128/6 |
| 4,503,842 | 3/1985 | Takayama | 128/4 |
| 4,530,568 | 7/1985 | Haduch et al. | 128/6 X |
| 4,617,914 | 10/1986 | Ueda | 128/4 |

Primary Examiner—William H. Grieb
Attorney, Agent, or Firm—Perman & Green

[57] ABSTRACT

An inspection instrument having a generally elongated flexible shaft extending between a control head at a proximal end and an objective assembly at a distal end. A bending section adjacent the objective assembly enables movement of the objective assembly between a neutral position and angularly disposed positions. A control member on the control head causes deflection of the objective assembly by means of a pair of operating cables which are operatively connected at their opposite ends to the control member and to the objective assembly. A compensating mechanism engages the cables intermediate their ends and is effective to guard the cable against excessive loads and also to readily accommodate variations in the working length of the cables as occurs when the cables are permanently stretched.

27 Claims, 12 Drawing Figures

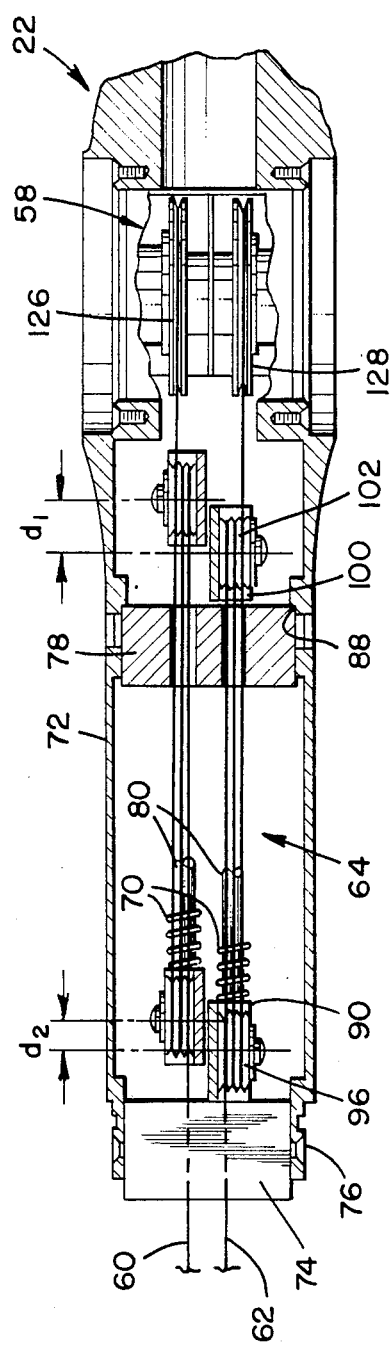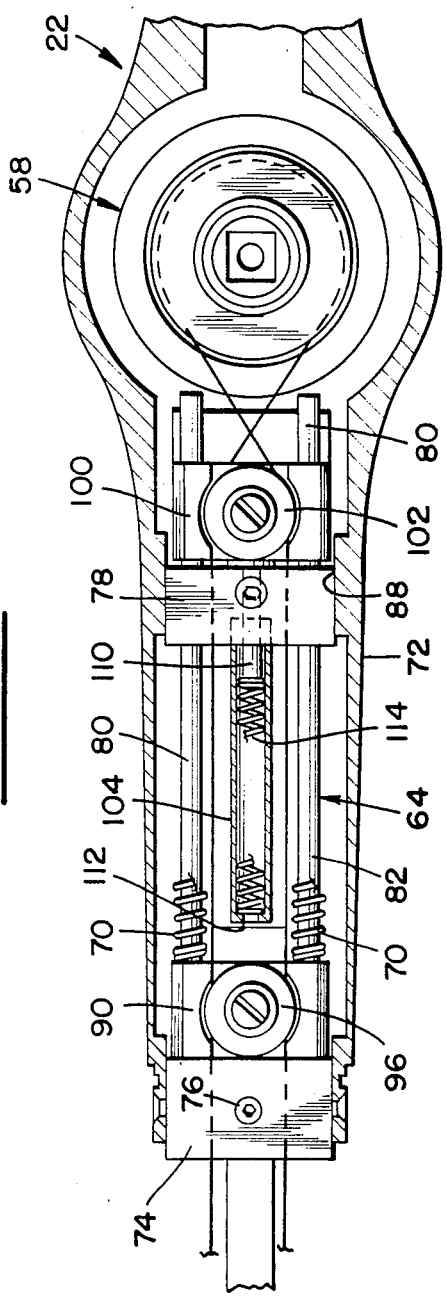

ENDOSCOPE WITH CABLE COMPENSATING MECHANISM

FIELD OF THE INVENTION

This invention relates to an elongated flexible inspection system for use in both industrial and medical applications and, more particularly, to a compensating mechanism for protecting operating cables against excessive tensile forces and adjusting slack in the operating cables.

BACKGROUND OF THE INVENTION

Endoscopes are well-known optical imaging devices used for viewing objects within cavities or the internal surfaces of cavities, with additional capabilities of providing channels for insertion of devices to act upon or treat conditions of interest found. While the herein described invention has application in many fields, it has particular relevance to the medical field wherein flexible endoscopes are employed to view and treat deep and convoluted passages of the human body.

In a typical endoscope designed for such purposes, the distal tip of the instrument is made maneuverable by employing two or more angularly spaced cables which interact mechanically with a series of vertebrated or specifically profiled rings located adjacent to the distal end of the instrument. Bending and deflection of the rings is obtained by tensioning and relaxing the cables in accordance with controls located at the proximal end of the endoscope on the control head. The means for applying tension and relaxing forces to these cables have been the subject of extensive technological effort resulting in controls such as joysticks or coaxial control wheels found on many well-known endoscopes. The object of these efforts has been to provide on the control head of the endoscope cable tensioning and relaxing means accessible and comfortable to the hands and fingers of the operator, and, consistent with holding the scope, operating all other controls, and allowing such other manipulations of the endoscope (i.e., torque, pushing and pulling) as are deemed effective for the clinical procedure for which the endoscope was designed.

Throughout this disclosure, it will be appreciated that the term "cable" is intended to refer to any elongate material which can be effectively utilized to operatively connect the distal end of the instrument to the control head. Thus, for purposes of the invention, wire, bands, chains and the like are considered to be equivalent to cables.

In the practice of medicine, a common form of such a device is used for inspection of the human ureter while a similarly structured device is used for inspection of the urethra and bladder. The endoscope is conventionally used in the diagnosis of tumors and other conditions in the urinary tract. The endoscopic examination involves the physician observing the urinary or vesical wall through an eyepiece in the control head of the instrument. Generally, the endoscope is provided with a source of illumination at its objective end, the end which is placed adjacent the area to be examined, and a bundle of light-transmitting fibers through which an image of the examined area is transmitted back to the eyepiece. The endoscope can further incorporate a channel which provides a washing fluid for application to the site under examination as well as a surgical tip and other features.

A factor to be considered in the construction of the endoscope for its normal medical use is its flexibility and articulation which permits the objective tip to be directed along the urinary tract. An endoscope can be made to traverse a considerable distance within this tract providing that any bends in the channel have a sufficiently large radius of curvature to enable the objective end of the endoscope to be readily articulated to follow the course of the tract. Care must be taken, however, to precisely guide the instrument so as not to puncture the vesical wall, especially as the device is being inserted.

The jet engine is one type of mechanical structure for which elongated tubular inpection devices, particularly such devices incorporating flexible fiber optics, have been found to be most useful, particularly to inspect the first stage, or high temperature stage, of the engine just behind the burner can which has components that are most subject to wear and deterioration. The arrangement of the jet engine's rotor and stator blades, particularly those in the high temperature stage of the engine, presents a most complex geometry which has not been amenable to inspection in the past other than by first disassembling the engine. There had previously been a need for some form of inspection device which could be placed near the rotor and stator blades, and other important sites within the engine, for the inspection thereof without the laborious task of disabling the engine. The use of this type of instrument has effected substantial savings in the cost of maintenance of the engines. Savings have resulted from the reduced man-hours achieved by avoiding the disassembly and reassembly of the engine. Additional savings have resulted from the increase in service time of the engine since the downtime for maintenance has been substantially reduced.

While the state of the art relating to endoscopes is relatively advanced today, there are still recurring problems which result when excessive stresses are applied to the operating cables by the hand operated control mechanism. In an extreme situation, this can result in breakage of the cable or, in a less extreme situation, to permanently stretching the cable. In the former instance, the endoscope is rendered useless until the cable has been replaced. In a latter instance, the endoscope loses a portion of its original deflection capability, making it necessary to take up the slack of the stretched cable and recalibrate the instrument. In both instances, it is necessary to open the instrument, usually at the factory or at a well equipped service center, and perform the necessary operations to return the instrument to its former operating condition. This procedure, of course, results in considerable downtime thereby creating scheduling problems, possibly delaying for long periods of time critical inspection procedures which cannot be performed until the instrument has been repaired. This, of course, causes substantial frustration to the user and is economically detrimental.

SUMMARY OF THE INVENTION

It was with knowledge of the prior art and the problems existing which gave rise to the present invention. In brief, the present invention is directed toward an inspection instrument having a generally elongated flexible body extending between a control head at a proximal end and an objective assembly at a distal end. A bending section adjacent the objective assembly enables movement of the objective assembly between a neutral position and angularly disposed positions. A control member on the control head causes deflection of the objective assembly by means of a pair of operating cables which are operatively connected at their opposite ends to the control member and to the objective assembly. A compensating mechanism engages the cables intermediate their ends and is effective to guard the cables against excessive stresses and also to readily accommodate variations in the working length of the cables as occurs when the cables are stretched.

In the prior art, each operating cable has a direct movement relationship between the actuation lever and the deflecting tip. Any movement by either moving member causes a relative movement of the other member. If one member is constrained while the other is moved, the movement causes cable load, which in turn can cause cable stretch, cable failure, or even damage to another part of the system. To remedy this situation, one of the features of the invention comes into play. Under normal working conditions, this mechanism works the same as prior art mechanisms. However, if an excessive load is applied to the cable by the user (e.g., by restraining the deflecting tip and moving the actuating lever), a compensating mechanism converts a potential overload into a linear movement of a pulley assembly which provides the affected cables with the extra length required to complete its movement without moving the restrained end of the instrument.

Furthermore, in the prior art, when adjustment of the cable length is required, it is performed during the assembly of the instrument, customarily a turn-buckle and screw arrangement. During the life of an instrument, a stretching of the cable can occur, which results as free-play in the deflecting lever, and therefore a lack of full deflection of the distal end of the instrument in response to movement of the deflecting lever. To remedy this situation, as in the previous instance, the instrument must be disassembled in order to provide the necessary turn-buckle screw adjustment. According to another feature of the invention, an adjustment mechanism is provided which can take up any free working length of the cable during assembly or at any time thereafter by merely loosening and then retightening one screw which is accessible through the outer housing of the instrument. This adjustment can be performed by the operator of the instrument in the field without the necessity of returning the instrument to a service center.

Accordingly, the invention is of benefit in those instances where there is a possibility of overloading the operating cables of an inspection instrument or where it is desired to adjust the length of an operating cable, for example, in the event it has become stretched.

In a flexible endoscope deflection control constructed in accordance with the invention, the control head of the instrument is shaped and sized to be held by one hand while the deflection controls are so located as to be manipulatable by the fingers of the same hand. In this manner, the hand not engaged in holding and controlling the control head of the endoscope is freed to an optimum extent for the control of the flexible insertion shaft of the instrument to thereby achieve enhanced control and ease of manipulation.

Other and further features, objects, advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in, and constitute a part of, this invention illustrate one embodiment of the invention and, together with the description, serve to explain the principles of the invention in general terms. Throughout the drawings, like numerals refer to like parts.

BRIEF DESCRIPTION OF THE DRAWINGS

FIG. 4 is a detail top plan view, certain parts being cut away and in section, illustrating a part of the invention;

FIG. 5 is a detail side elevation view, certain parts being cut away and in section, generally of those portions illustrated in FIG. 4;

DESCRIPTION OF THE PREFERRED EMBODIMENT

Figure 1:
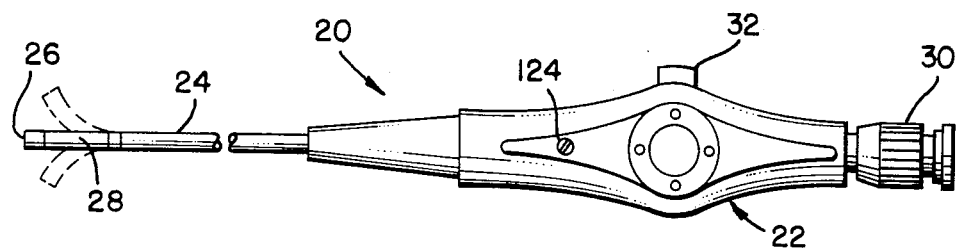
FIG. 1 is a side elevation view illustrating an elongated flexible inspection system embodying the invention.

Turn now to the drawings and initially to FIG. 1 which illustrates an endoscope 20 or other similar elongated flexible inspection instrument. As generally illustrated, the endoscope 20 has a control head 22, an elongated flexible shaft 24 terminating at an objective assembly 26 which is preceded by a suitable controlled bending section 28. Typically, the shaft 24 houses a fiber optical system which extends between the objective assembly 26 at a distal end of the endoscope 20 and an eyepiece 30 mounted on the control head 22. However, it will be understood that the shaft 24 could alternately contain a conventional lens system should that be desirable. It is through the eyepiece 30 that the operator observes the object being examined. A control member 32 is pivotally mounted on the control head 22 in a manner which will be more completely described below and is effective to move the objective assembly 26 between a position which is generally axially aligned with a central axis of the body 24 and at least one of the positions angularly disposed relative thereto as illustrated by dotted lines in FIG. 1.

Figure 2:
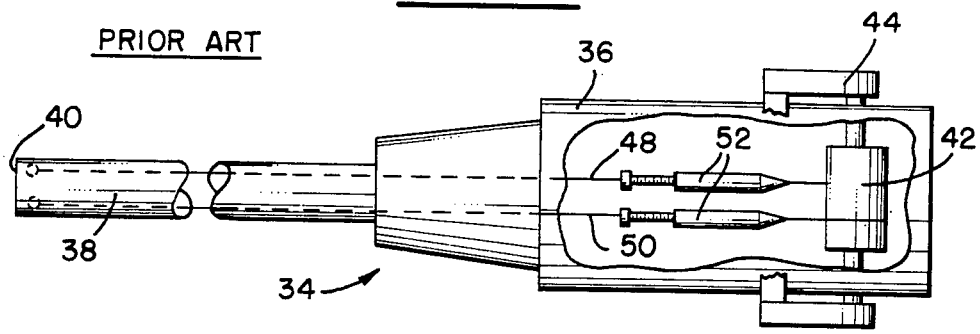
FIG. 2 is a top plan view, certain portions being cut away, of an inspection system known to the prior art.

As previously noted, the invention is intended for use in endoscopes and the like with a deflecting tip or objective assembly where the objective assembly is actuated by a control cable. The invention has a two fold function. First, it limits the amount of load that can be applied to the control cable; and second, it provides a simple method of taking up the free working length of the same cable. FIG. 2 is representative of a typical prior art construction. As shown in FIG. 2, such a conventional endoscope 34 is seen to comprise a control head 36 and an elongated flexible body 38 terminating at a objective assembly 40. Through an appropriate control mechanism 42 located within the control head 36, a control handle 44 operate control cables 48 and 50, respectively, to thereby deflect the objective assembly 40 in one direction or another, as desired.

However, it will be appreciated that in the construction of the conventional endoscope 34, there is a direct movement relationship between the control handle 44 and the objective assembly 40. That is, any movement by the control handle 44 is imparted to the objective assembly 40, and vice versa. Similarly, if one of these elements is constrained while the other is moved, the movement will impart to the cables 48, 50 stresses which are substantially greater than normal. In turn, this condition can cause cable stretch, cable failure, or even damage to another part of the system. Such a situation can occur, for example, when a stiff accessory is used, or when the objective assembly 40 bears against an object to be viewed, and the operator moves the control handle 44 in an attempt to dislodge the object or move the objective assembly 40 past the object.

In times past, the remedy for such an occurrence required major servicing of the endoscope. Users of endoscopes do not customarily have the equipment or personnel to repair these sophisticated instruments, so they must be returned to a qualified service facility thereby causing loss to the user by reason of the unavailability of the instrument, possibly for an extended period of time. Thereupon, even at an equipped facility, the endoscope would have to be disassembled, cables or other damaged parts replaced, then reassembled. In the event the only problem with an instrument was that one or both of the cables 48, 50 had been stretched, then it would be necessary to take up the slack in the cables by means of turnbuckles 52 which were integrally attached to the cables for this purpose. This is a time consuming and costly process and takes the instrument out of commission until it is repaired.

Figure 3:
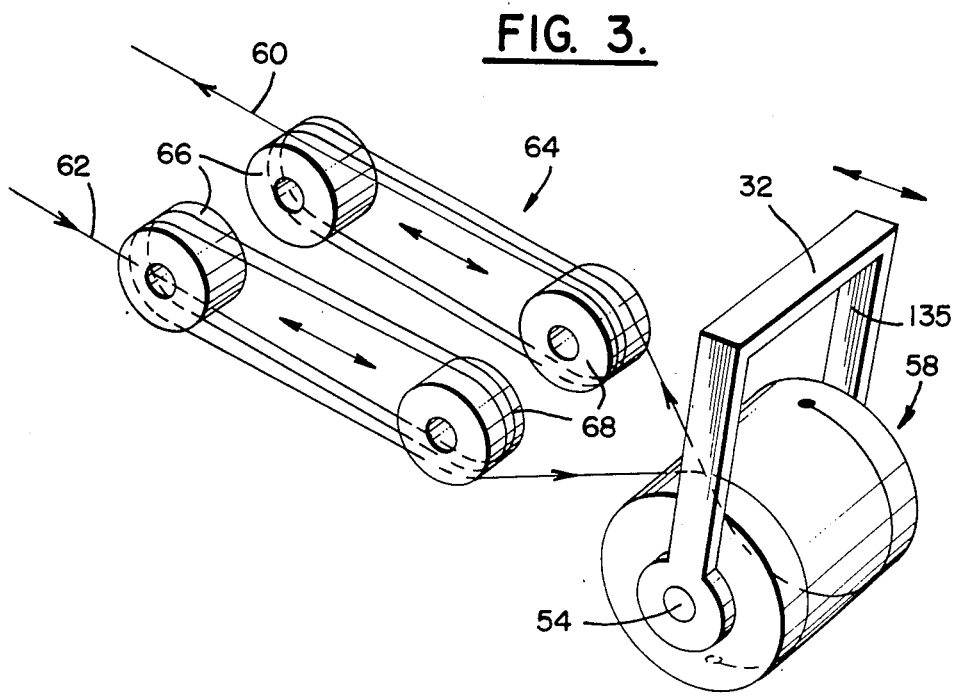
FIG. 3 is a perspective diagrammatic view of a compensating mechanism employed by the invention.

The present invention serves to eliminate the undesirable operational aspects of the prior art as just described. FIG. 3 is a diagramatic illustration of a construction embodying the invention which serves as such an improvement. As shown in FIG. 3, the control member 32 can be pivoted to and fro about an axis 54 and generally in the directions indicated by a double arrow head 56. The arcuate movement of the control lever 32 is imparted, by a control mechanism 58, to a pair of control cables 60 and 62, respectfully, which terminate distal to the objective assembly 26. However, the control cables 60, 62 are intercepted as they proceed from the control mechanism 58 to the objective assembly by respective compensating mechanisms 64. Each compensating mechanism comprises first and second spaced apart cable guides in the form of pulleys 66 and 68 around which the control cables 60 and 62 are collectively wound. That is, as seen in FIG. 3, each of the cables 60 and 62 is wound around its respective pair of pulleys 66, 68 two and a half times before it continues on toward the distal end of the endoscope 20. It will be appreciated that the number of loops formed by the cables 60, 62 is not critical for the purposes of the invention but are determined by design requirements.

In the course of the operation of the invention, as excessive stress is applied to the cables 60 and 62, the pulleys 66 are caused to move against the bias of first pre-loaded compression springs 70 (see FIGS. 4, 5, and 6) and in the direction of the second pulleys 68. The spring rate of each spring 70 and the number of loops formed by the cables determines the maximum load on the cables 60 and 62. That is, when that magnitude of load is reached, then the compensating mechanism 64 makes available an additional length of cable at the maximum value of tensile load being experienced by the cables. A specific construction which permits this movement will be described below in greater detail. Additionally, in the event the endoscope 20 experiences slack in the cables 60 and 62, the pulleys 68 can be moved in a direction away from the pulleys 66 to thereby take up such slack. Furthermore, this operation can be readily accomplished by the user without the necessity of returning the instrument to a repair facility. Again, a construction enabling this operation will be described below.

Continue now with reference again especially to FIGS. 4, 5, and 6. The control head 22 includes a generally cylindrical control housing 72 which encompasses the control mechanism 58 and the compensating mechanism 64. A chassis block 74 is suitably attached, as by fasteners 76 to a distal end of the control housing 72 so as to be operatively integral therewith. A guide block 78 is supported by the control housing 72 intermediate the chassis block 74 and the control mechanism 58.

Figure 6:
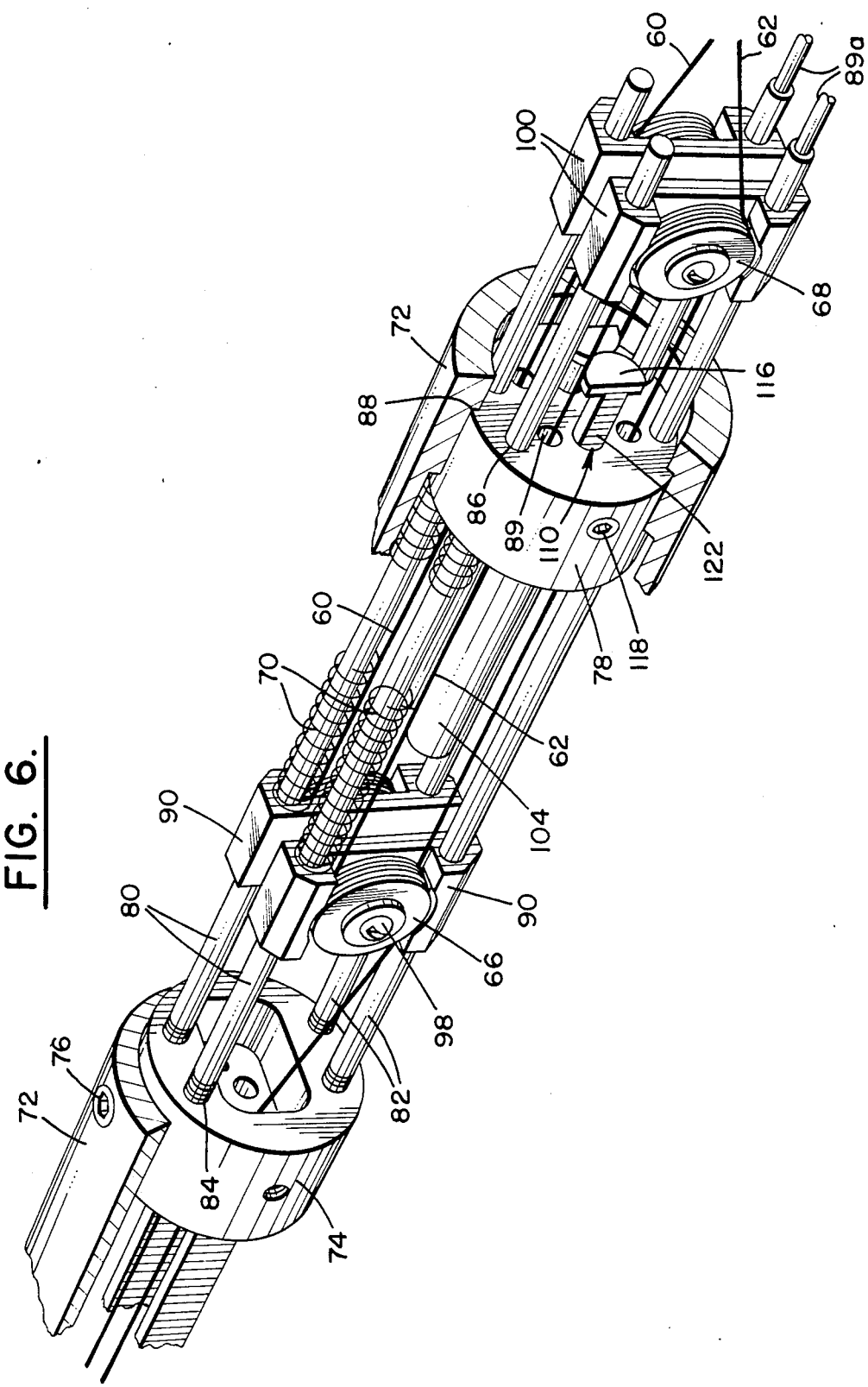
FIG. 6 is a detail perspective view illustrating the compensating mechanism of the invention.

A pair of parallel, spaced apart rods 80 and 82 associated with each of the cables 60 and 62 are fixed at spaced locations, to the chassis block 74 and to the guide block 78. For example, ends of the rods 80 and 82 may be threadedly engaged with tapped bores 84 in the chassis block 74 (FIG. 6). Additionally, the rods 80 and 82 can be fittingly received within smooth bores 86 in the guide block 78 such that they extend through and beyond the guide block in the direction of the control head 22. By reason of this construction, the guide block 78 is held firmly in position against an annular shoulder 88. Also, it will be appreciated that the cables 60 and 62 extend freely through axially directed passages 89 in the guide block 78 and through similar passages not shown in the chassis block 74. As seen especially in FIGS. 6 and 8, the rods 80 are tubular and receive therethrough fiber optic bundles 89a as they pass through the control head 22.

A pair of first carriage members 90 positioned in side by side relationship and associated with each of the control cables 60 and 62 are slideably received on the rods 80 and 82 as is particularly well seen in FIG. 6. The first carriage members 90 are positioned between chassis block 74 and the guide block 78 and are engaged by and biased pre-loaded onto the chassis block by means of the springs 70 which encircle and are supported by the rods 80.

Figure 7:
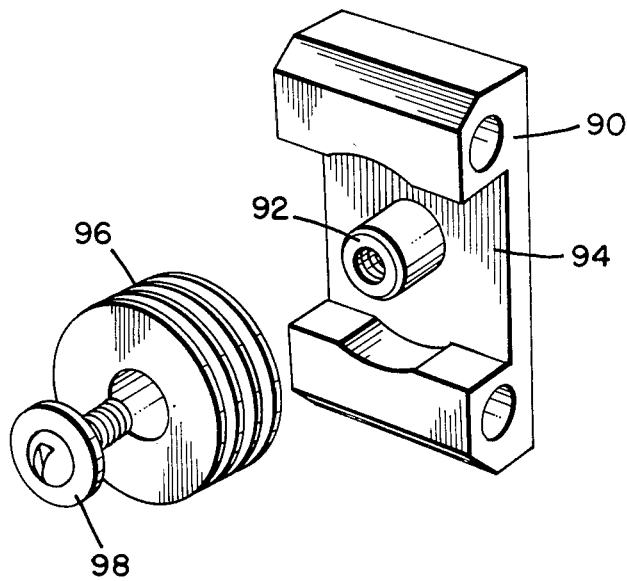
FIG. 7 is a detail exploded perspective view of a pully and carriage assembly utilized by the invention.

As seen in FIG. 7, each of the carriage members 90 is provided with an integral stub shaft 92 which extends transversely through a recessed region 94. A first compensator pulley 66 (equivalent to the pulleys 66 illustrated in FIG. 3) is rotatably mounted on the stub shaft 92 and held rotatably in position thereon by means of a suitable retainer lug 98.

In a similar fashion, a pair of second carriage members 100 are slideably mounted on the rods 80 between the guide block 78 and the control mechanism 58. Second compensator pulleys 68 (equivalent to the pulleys 68 illustrated in FIG. 3) are rotatably mounted on their associated carriage members 100 just as the pulleys 66 are rotatably mounted on their associated carriage members 90. It will be appreciated that in each instance, the axis of rotation for the pulleys 66 and 68 extends in a direction generally transverse of the control cables 60 and 62. As previously explained, each of the cables 60 and 62 is looped at least once around each of its associated pulleys 66 and 68, collectively, as it extends between the control mechanism 58 and the objective assembly 40.

The compensating mechanism 64 which has just been described insures that the control cables 60 and 62 will not be subjected to a tensile load in excess of a predetermined magnitude, as determined by the spring rate of the springs 70. The springs, of course, can be replaced by others having different spring rates and therefore, allow a different tensile load to occur in the control cables 60 and 62 should that be desired. In any event, during the operation of the endoscope 20, should the tensile load in a cable exceed a predetermined value, which would occur, for example, if the objective assembly 40 was prevented from moving while the control lever 32 continued to be moved by the operator. In that event, the carriage 90 associated with a particular one of the control cables would move along the rods 80 and against the bias of the springs 70 to thereby shorten the distance between the pulleys 66 and 68. By so doing, the working length of the control cable is extended to accommodate the continued motion of the control lever while avoiding damage to the control cable or to any other component of the endoscope.

Figure 8:
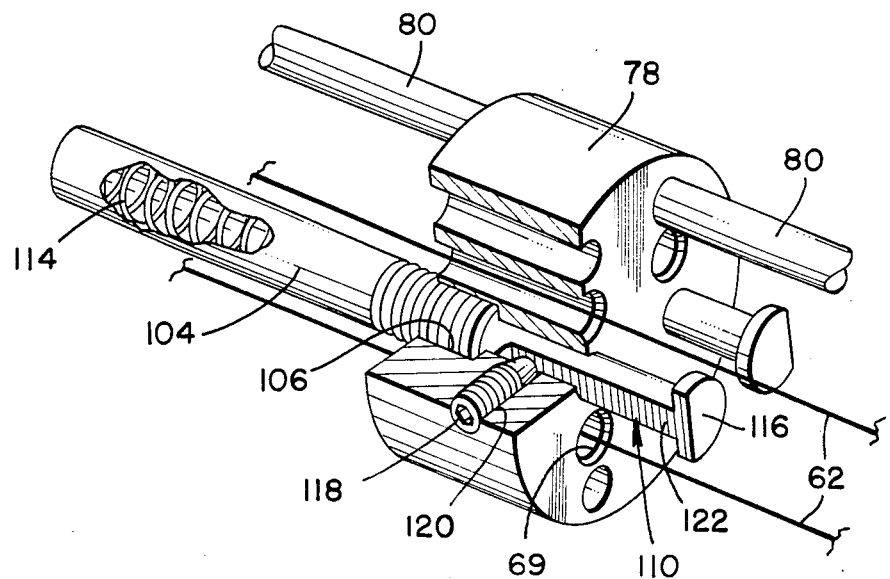
FIG. 8 is a detail perspective view, certain parts being cut away and in section, illustrating a mechanism for adjusting the slack in a control cable.

A construction operable to prevent the occurrence of slack in the cables 60 and 62 will now be described with particular reference to FIG. 8 and continuing reference to FIGS. 5 and 6. A generally cylindrical internal or spring housing 104 associated with each of the cables 60 and 62 is suitably mounted on the guide block 78 and extends generally parallel to and spaced from the rods 80 and 82 in the direction of the chassis block 74. The mounted end of the housing 104 may be threadly engaged with a tapped bore 106 in the guide block 78. Within the guide block 78, the tapped bore 106 communicates with a smooth bore 108 which slideably receives therein a plunger 110. A free end of the housing 104 is provided with a shoulder 112 (FIG. 5) which supports one end of a compression spring 114. The other end of the compression spring engages an internal end of the plunger 110 and biases the plunger to the right as seen in FIGS. 5, 6, and 8. A free end of the plunger 110 has a broadened abutment face 116 thereon which serves to engage an associated carriage member 100. It will be appreciated that even when the cables 60 and 62 are in their relaxed condition, their tension is such as to draw the carriage members 100 to the left (viewing FIGS. 4, 5, and 6) toward the guide block 78 and into engagement with abutment face 116. Simultaneously, the spring 114 which is designed to have a spring rate less than that of the springs 70 urges the plunger 110 to the right (viewing FIGS. 4, 5, 6, and 8) such that the abutment face 116 engages the carriage member 100.

Figure 9:
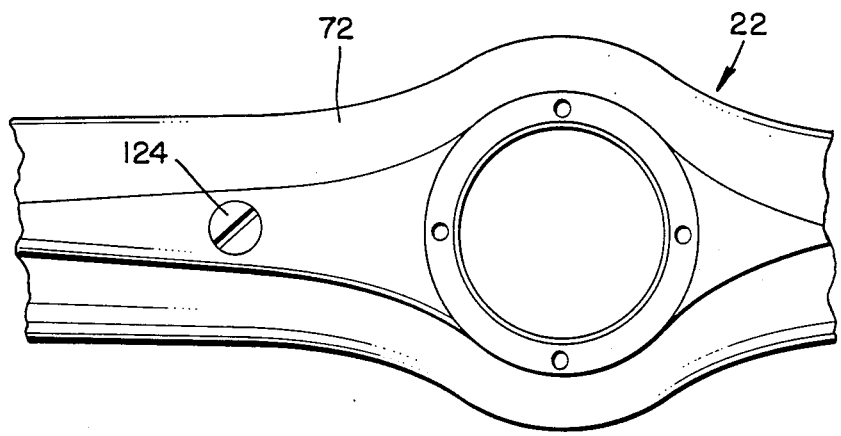
FIG. 9 is a detail side elevation view of a portion of a control housing for the invention.

During initial fabrication of the endoscope 20, when an equilibrium position between the plunger 110 and its associated carriage member 100 is achieved, the plunger 110 is selectively held against further movement relative to the guide block 78. This is achieved by means of a screw 118 which is threadly engaged with a radial tapped bore 120 formed in the guide block 78 and communicating with a flattened surface or region 122 formed on the plunger 110 and generally facing the tapped hole. Subsequently, should the cable 60 or 62 become stretched such that the pulleys 66 and 68 no longer properly engage the cable, the operator can readily correct the situation and immediately thereafter put the endoscope to its intended use. Specifically, this can be achieved by removing a cap 124, or other suitable cover, on the housing 72 (see FIG. 9) aligned with the set screw 118. The operator then releases the set screw 118 from engagement with the flattened region 122 allowing the spring 114 to move the plunger 110 which pushes the carriage 100 so that the pulley 68 once again engages its associated control cable. This operation, in turn, draws all strands looped around the pulleys 66 and 68, collectively, into the normal taut condition. When this is accomplished, set screw 118 is again tightened into engagement with the flattened region 122, and the cap 124 is replaced on the housing 72.

In FIG. 4, the carriage members 90 and 100 nearest the reader and their respective pulleys 66 and 68 associated with the control cable 62 are illustrated at their extreme or hard left positions. That is, the carriage member 90 is hard against the chassis block 74 and the carriage member 100 is hard against the abutment face 116 which, in turn, is at its extreme left hand position against the guide block 78. At the same time, in FIG. 4, the carriage members 90 and 100 farthest from the reader and their respective pulleys 66 and 68 associated with the control cable 60 are illustrated at their typical working positions. That is, the carriage member 100 is shown positioned to the right a distance $d_1$ which presumably is necessary for its associated pulley 68 to engage the cable 60 and is held in that position by the plunger 110. The carriage member 90 is shown positioned to the right a distance $d_2$ which results from the tension in the cable 60 which imparts compression to the spring 70.

Figure 10:
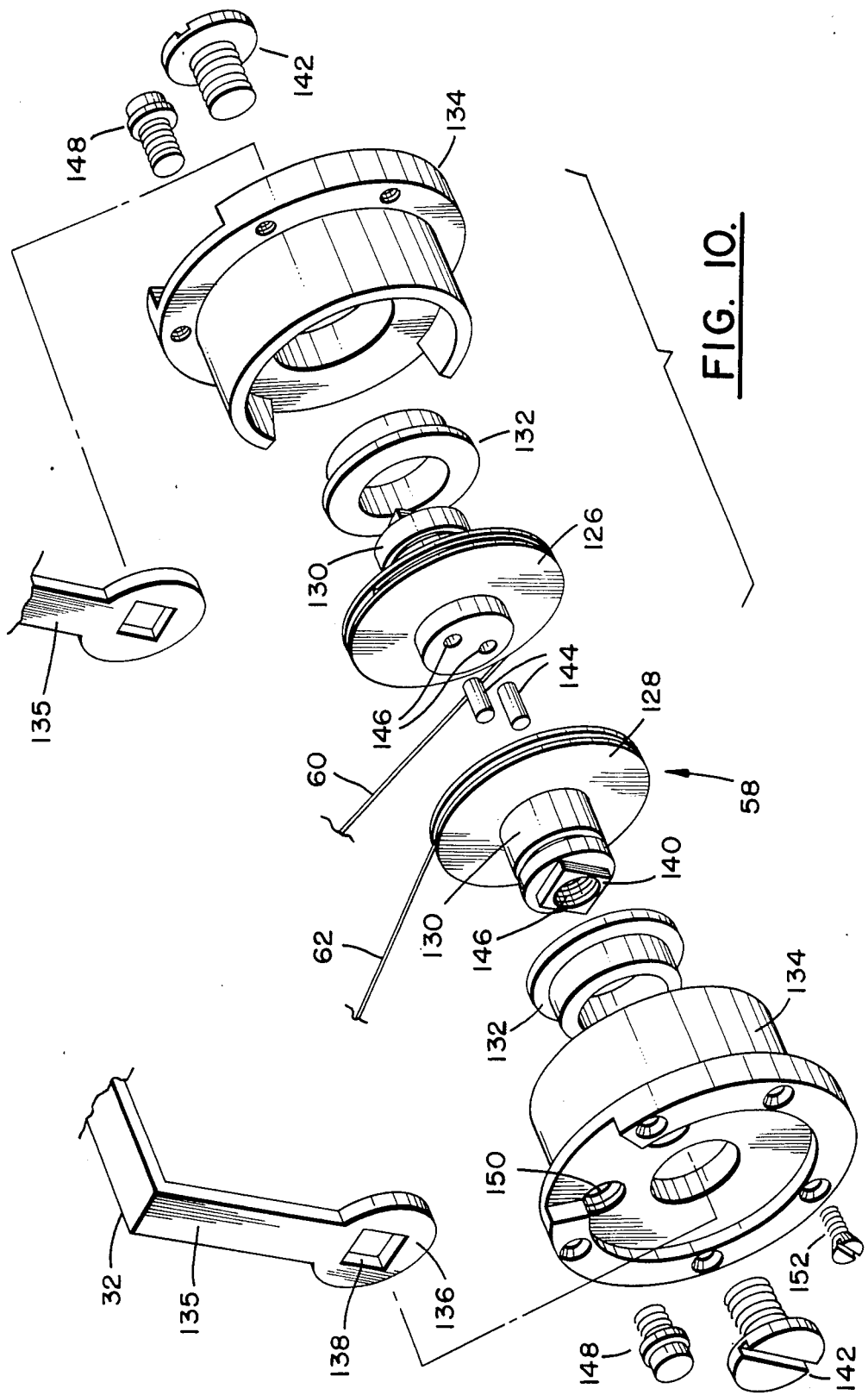
FIG. 10 is a detail exploded view, in perspective, illustrating a control mechanism utilized by the invention.
Figure 11:
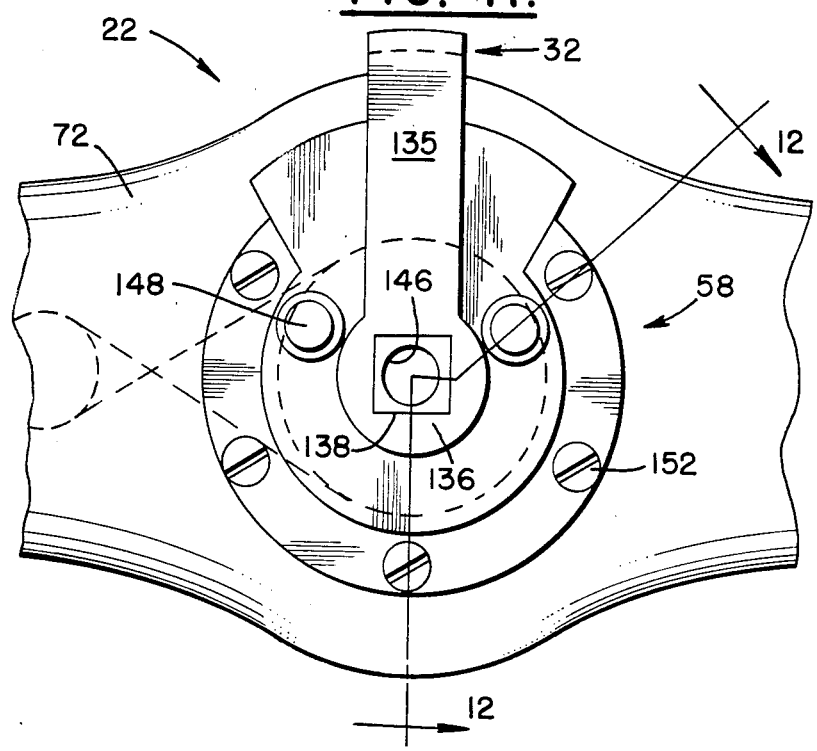
FIG. 11 is a detail side elevation view generally illustrating the control head utilized by the invention.
Figure 12:
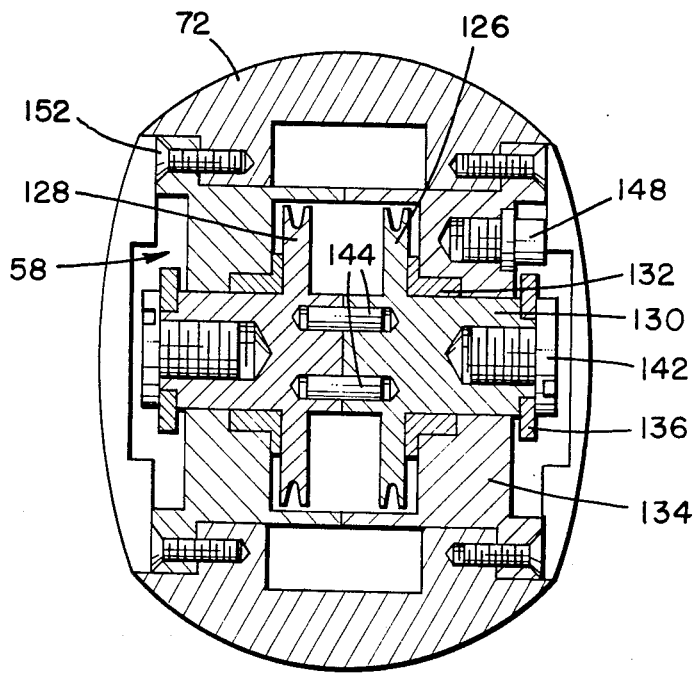
FIG. 12 is a cross section view taken generally along line 12—12 in FIG. 11.

Turn now to FIGS. 10, 11, and 12 for a detailed description of the control mechanism 58. The heart of the control mechanism 58 is a pair of control pulleys 126 and 128 associated with the control cables 60 and 62, respectively. By way of an integral stub shaft 130, journal bearing 132 and pulley housing 134 associated with each pulley, the pulleys 126 and 128 are rotatably mounted on the control head 22 about a common transverse axis extending generally parallel to the axes of the compensator pulleys 66 and 68. As best illustrated in FIGS. 3 and 10, the control cable 62 is attached at its end to the control pulley 128 and extends around the control pulley in a counter-clockwise direction as it extends toward its associated one of the compensator pulleys 68. In a similar fashion, the control cable 60 is suitably attached at its end to control pulley 126 and extends around that pulley in a clockwise direction toward its associated one of the compensator pulleys 68.

The control lever 32 is bifurcated so as to have a pair of parallel depending legs 135 which terminate at enlarged ends 136 formed with key slots 138. The key slots 138 fittingly receive keys 140 formed at the extremity of each of the stub shafts 130 on the pulleys 126 and 128. In turn, large screws 142 are threadly received in tapped bores 146 within the stub shafts 130 to hold the entire assembly together. A pair of pins 144 are fittingly received in smooth bores 146 to assure that the pulleys 126 and 128 will rotate as a unit upon operation of the lever 32. Cylindrical shaped lever stops 148 are threadly received in appropriately located tapped bores 150 in each pulley housing to thereby define the limits of arcuate travel of the lever 32. The entire control mechanism 58 is mounted to the control housing 72 by means of assembly screws 152.

While a preferred embodiment of the invention has been disclosed in detail, it should be understood by those skilled in the art that various other modifications may be made to the illustrated embodiment without departing from the scope as described in the specification and defined in the appended claims.

I claim:

1. An inspection instrument having a generally elongated flexible shaft extending between a control head at a proximal end thereof and an objective assembly at a distal end thereof comprising:
   a controlled bending section adjacent said objective assembly enabling movement of said objective assembly between a position generally axially aligned with said elongated flexible shaft, and positions angularly disposed relative thereto;
   a control member movably mounted on said control head;
   at least one operating cable means extending between said proximal end and said distal end, said operating cable means being operatively connected at its opposite ends to said objective assembly and to said control member for deflecting said objective assembly in at least one direction; and
   compensating means engageable with each of said cables intermediate said opposite ends thereof operable for preventing a tensile force in said cables in excess of a predetermined value or for accommodating variations in the working length of said cables.

2. An inspection instrument as set forth in claim 1 including an image transmitting optical system intermediate said control head and said objective assembly for viewing subject matter to be inspected.

3. An inspection instrument as set forth in claim 2 wherein said optical system is a fiber optical system.

4. An inspection instrument as set forth in claim 2 wherein said optical system is a rigid optical system.

5. An inspection instrument as set forth in claim 2 wherein said optical system is an electronic imaging system.

6. An inspection instrument as set forth in claim 1 wherein said compensating means for each of said cables includes:
   first and second spaced apart cable guides extending across the path of said cable, said cable being engageably looped at least once around said first and second cable guides collectively as it extends between said control member and said objective assembly;
   said second cable guide having a normally positionally fixed axis;
   said first cable guide having an axis movable between a first position distant from said second cable guide and a second position nearer to said second cable guide; and
   first resilient means biasing said first cable guide toward said first position.

7. An inspection instrument as set forth in claim 1 including:
   a generally cylindrical control housing encompassing said control head and said compensating means;
   a chassis block fixed to said housing distant from said control head;
   a guide block supported by said control housing intermediate said chassis block and said control head;
   a pair of parallel, spaced apart rods associated with each of said cables, said rods being fixed at spaced locations, respectively, to said chassis block and to said guide block and extending through and beyond said guide block in the direction of said control head;
   a first carriage member slidably received on said rods intermediate said chassis block and said guide block;
   a first compression spring received on each of said rods and extending between said first member and said guide block thereby biasing said first carriage member against said chassis block;
   a second carriage member slidably received on said rods intermediate said guide block and said control head;
   a first compensator pulley rotatably mounted on said first carriage member on an axis extending transversely of said cable; and
   a second compensator pulley rotatably mounted on said second carriage member on an axis extending transversely of said cable;
   said cable being looped at least once around said first and second cable compensator pulleys collectively as it extends between said control member and said objective assembly;
   whereby excessive tensile force applied to said cable upon operation of said control member causes said first carriage member to move against the bias of said first compression springs toward said guide block.

8. An inspection instrument as set forth in claim 7 including:
   a generally cylindrical spring housing associated with each of said cables, said spring housing mounted at one end to said guide block and extending generally parallel to and spaced from said rods and having a shoulder at a free end distant from said guide block;
   said guide block having a bore therethrough axially aligned with said spring housing;
   a plunger slidably received in the bore having one end engageable with said second carriage member and an opposite end extending into said spring housing;
   a second compression spring within said spring housing extending between said plunger and said shoulder on said free end of said spring housing thereby biasing said second compensator pulley firmly into engagement with said cable to counteract the occurrence of slack in said cable between said first and second compensator pulleys.

9. An inspection instrument as set forth in claim 8 including:
   fastener means on said guide block engageable with said plunger for selectively positioning said plunger relative to said guide block to thereby take up any slack in said cable.

10. An inspection instrument as set forth in claim 9 wherein said guide block has a radially extending tapped bore and wherein said fastener means is a set screw threadedly engaged with the tapped bore; and
   wherein said plunger includes a flattened region generally facing the tapped hole;

whereby said screw is engageable with said flattened region to selectively fix said plunger relative to said guide block.

11. An inspection instrument as set forth in claim 9 wherein said control member includes:
first and second control pulleys rotatably mounted on said control head about a common transverse axis extending generally parallel to the axes of said first and second compensator pulleys;
one of said cables being attached at its end to said first control pulley and extending around said first control pulley in a counterclockwise direction as it extends toward its associated one of said second compensator pulleys; and
the other of said cables being attached at its end to said second control pulley and extending around said second control pulley in a clockwise direction toward its associated one of said second compensator pulleys.

12. An inspection instrument as set forth in claim 11 wherein said control member includes:
an operating handle fixed to said first and second control pulleys for rotating said control pulleys simultaneously about said common transverse axis;
whereby rotation of said handle in one direction causes said one of said cables to advance and said other of said cables to retract with resultant deflection of said objective assembly in one direction; and
whereby rotation of said handle in the other direction causes said other of said cables to retract and said one of said cables to advance with resultant deflection of said objective assembly in an opposite direction.

13. An inspection instrument as set forth in claim 8 wherein the spring rate of said second compression spring is less than that of said first compression springs.

14. An inspection instrument as set forth in claim 1 including:
a chassis block integral with said control head and spaced therefrom in the direction of said objective assembly;
a control housing encompassing said chassis block and said control head;
a guide block supported by said control housing intermediate said chassis block and said control head;
guide means associated with each of said cables and extending between said chassis block and said control head;
a first carriage member slidably received on said guide means intermediate said chassis block and said guide block;
first resilient means on said guide means biasing said first carriage member toward said chassis block;
a first compensator pulley rotatably mounted on said first carriage member on an axis extending transversely of said cable;
a second carriage member slidably received on said guide means intermediate said guide block and said control head;
a second compensator pulley rotatably mounted on said second carriage member on an axis extending transversely of said cable;
said cable extending from said control member, then around said first and second compensator pulleys, collectively, then to said objective assembly;
whereby excessive tensile force applied to said cable upon operation of said control member causes said first carriage member to move against the bias of said first resilient means toward said guide block.

15. An inspection instrument as set forth in claim 14 including:
an internal housing associated with each of said cables mounted at one end to said guide block and extending generally parallel to said cables and having a shoulder thereon distant from said guide block;
said guide block having a bore therethrough axially aligned with said internal housing;
a plunger slidably received in the bore having one end engageable with said second carriage member and an opposite end extending into said internal housing;
second resilient means within said internal housing extending between said plunger and said shoulder on said free end of said internal housing;
thereby biasing said second compensator pulley firmly into engagement with said cable to counteract the occurence of slack in said cable between said first and second compensator pulleys.

16. An inspection instrument as set forth in claim 1 wherein said compensating means for each of said cables includes:
first and second spaced apart cable guides extending across the path of said cable, said cable being engageably looped at least once around said first and second cable guides collectively as it extends between said control member and said objective assembly;
fastener means being selectively movable between a normally tightened condition holding said second guide means positionally fixed on said instrument and a loosened condition to enable said first guide means to reengage said cable in the event of a variation in the length of said cable, said fastener means being returned to a tightened condition when said second guide means again engages said cable.

17. An inspection instrument as set forth in claim 16 including resilient means biasing said second guide means into engagement with said cable.

18. An inspection instrument as set forth in claim 7 wherein said rods are tubular; and
wherein said optical system is a fiber optical system which extends from said objective assembly to said control head and through one of said rods as it extends through said control housing.

19. An inspection instrument as set forth in claim 1 including:
a pair of operating cables extending between said proximal end and said distal end, each of said operating cables being operatively connected at its opposite ends to said objective assembly and to said control member for deflecting said objective assembly in at least two discrete directions.

20. An inspection instrument as set forth in claim 1 including:
four operating cables extending between said proximal end and said distal end, each of said operating cables being operatively connected at its opposite ends to said objective assembly and to said control member for deflecting said objective assembly in at least four discrete directions.

21. An inspection instrument as set forth in claim 1 wherein said compensating means includes a preload mechanism for rendering ineffective operation of said compensating means until the predetermined value of tensile force in said cables has been exceeded.

22. An inspection instrument as set forth in claim 21 wherein said preload mechanism is a spring.

23. An inspection instrument having a generally elongated flexible shaft extending between a control head at a proximal end thereof and a deflectible tip at a distal end thereof comprising:

a controlled bending section adjacent said deflectible tip enabling movement of said tip between a position generally axially aligned with said elongated flexible body and a position angularly disposed relative thereto;

a control member movably mounted on said control head;

an operating cable means extending between said proximal end and said distal end, said operating cable means being operatively connected at its opposite ends to the region of said deflectible tip and to said control member for deflecting said deflectible tip in at least one direction; and compensating means engageable with said cable intermediate said opposite ends thereof operable for preventing a tensile force in said cable in excess of a predetermined value or for accommodating variations in the working length of said cable.

24. An inspection instrument as set forth in claim 23 wherein said compensating means for said cable includes:

first and second spaced apart cable guides extending across the path of said cable, said cable being engageably looped at least once around said first and second cable guides collectively as it extends between said control head and said deflectible tip;

said second cable guide having a normally positionally fixed axis;

said first cable guide having an axis movable between a first position distant from said second cable guide and a second position nearer to said second cable guide; and first resilient means biasing said first cable guide toward said first position.

25. An inspection instrument as set forth in claim 23 including:

a chassis block integral with said control head and spaced therefrom in the direction of said objective assembly;

a control housing encompassing said chassis block and said control head;

a guide block supported by said control housing intermediate said chassis block and said control head;

guide means associated said cable means and extending between said chassis block and said control head; a first carriage member slidably received on said guide means intermediate said chassis block and said guide block;

first resilient means on said guide means biasing said first carriage member toward said chassis block;

a first compensator pulley rotatably mounted on said first carriage member on an axis extending transversely of said cable;

a second carriage member slidably received on said guide means intermediate said guide block and said control head;

a second compensator pulley rotatably mounted on said second carriage member on an axis extending transversely of said cable means;

said cable means extending from said control member, then around said first and second compensator pulleys, collectively, then to said deflectible tip;

whereby excessive tensile force applied to said cable means upon operation of said control member causes said first carriage member to move against the bias of said first resilient means toward said guide block.

26. An inspection instrument as set forth in claim 23 wherein said compensating means for each of said cables includes:

first and second spaced apart cable means guides extending across the path of said cable means, said cable means being engageably looped at least once around said first and second cable means guides collectively as it extends between said control head and said deflectible tip;

fastener means being selectively movable between a normally tightened condition holding said second guide means positionally fixed on said instrument and a loosened condition to enable said first guide means to reengage said cable means in the event of a variation in the length of said cable means, said fastener means being returned to a tightened condition when said second guide means again engages said cable means.

27. An inspection instrument as set forth in claim 23 including resilient means biasing said second guide means into engagement with said cable means.

* * * * *